(12) United States Patent
Miyano et al.

(10) Patent No.: US 7,072,504 B2
(45) Date of Patent: Jul. 4, 2006

(54) IMAGE SYNTHESIS APPARATUS

(75) Inventors: Naoki Miyano, Osaka (JP); Eiji Shimizu, Takatsuki (JP)

(73) Assignee: Sharp Kabushiki Kaisha, Osaka (JP)

( * ) Notice: Subject to any disclaimer, the term of this patent is extended or adjusted under 35 U.S.C. 154(b) by 617 days.

(21) Appl. No.: 09/788,497

(22) Filed: Feb. 21, 2001

(65) Prior Publication Data
US 2001/0046316 A1  Nov. 29, 2001

(30) Foreign Application Priority Data
Feb. 21, 2000  (JP)  ............................. 2000-043658
Feb. 19, 2001  (JP)  ............................. 2001-042405

(51) Int. Cl.
*G06K 9/00* (2006.01)

(52) U.S. Cl. ...................... 382/154; 345/419

(58) Field of Classification Search ................ 382/154, 382/282, 284, 285, 128; 345/419, 427; 356/12, 356/22, 51; 359/462, 464, 465; 374/121, 374/124; 250/339.02, 339.06, 339.11, 363.02, 250/363.04, 370.08
See application file for complete search history.

(56) References Cited

U.S. PATENT DOCUMENTS

| 5,124,915 A | * | 6/1992 | Krenzel | 702/5 |
| 5,129,010 A | * | 7/1992 | Higuchi et al. | 382/154 |
| 6,219,462 B1 | * | 4/2001 | Anandan et al. | 382/294 |
| 6,396,946 B1 | * | 5/2002 | Sogawa | 382/154 |
| 6,556,858 B1 | * | 4/2003 | Zeman | 600/473 |
| 6,597,807 B1 | * | 7/2003 | Watkins et al. | 382/164 |
| 6,640,130 B1 | * | 10/2003 | Freeman et al. | 600/474 |

FOREIGN PATENT DOCUMENTS

| JP | 05-122602 | 5/1993 |
| JP | 05-223551 | 8/1993 |
| JP | 09220203 | 8/1997 |
| JP | 10-188034 | 7/1998 |
| JP | 11-098537 | 4/1999 |

* cited by examiner

*Primary Examiner*—Samir Ahmed
(74) *Attorney, Agent, or Firm*—Birch, Stewart, Kolasch & Birch, LLP

(57) ABSTRACT

An image synthesis apparatus includes a right infrared camera and a left infrared camera; a right visible light camera and a left visible light camera; and a first image synthesis processing device for synthesizing data output from the right infrared camera and from the left infrared camera and data output from the right visible light camera and from the left visible light camera so that a three-dimensional thermal image and a three-dimensional visible light image are observed by an observer as overlapping each other.

11 Claims, 11 Drawing Sheets

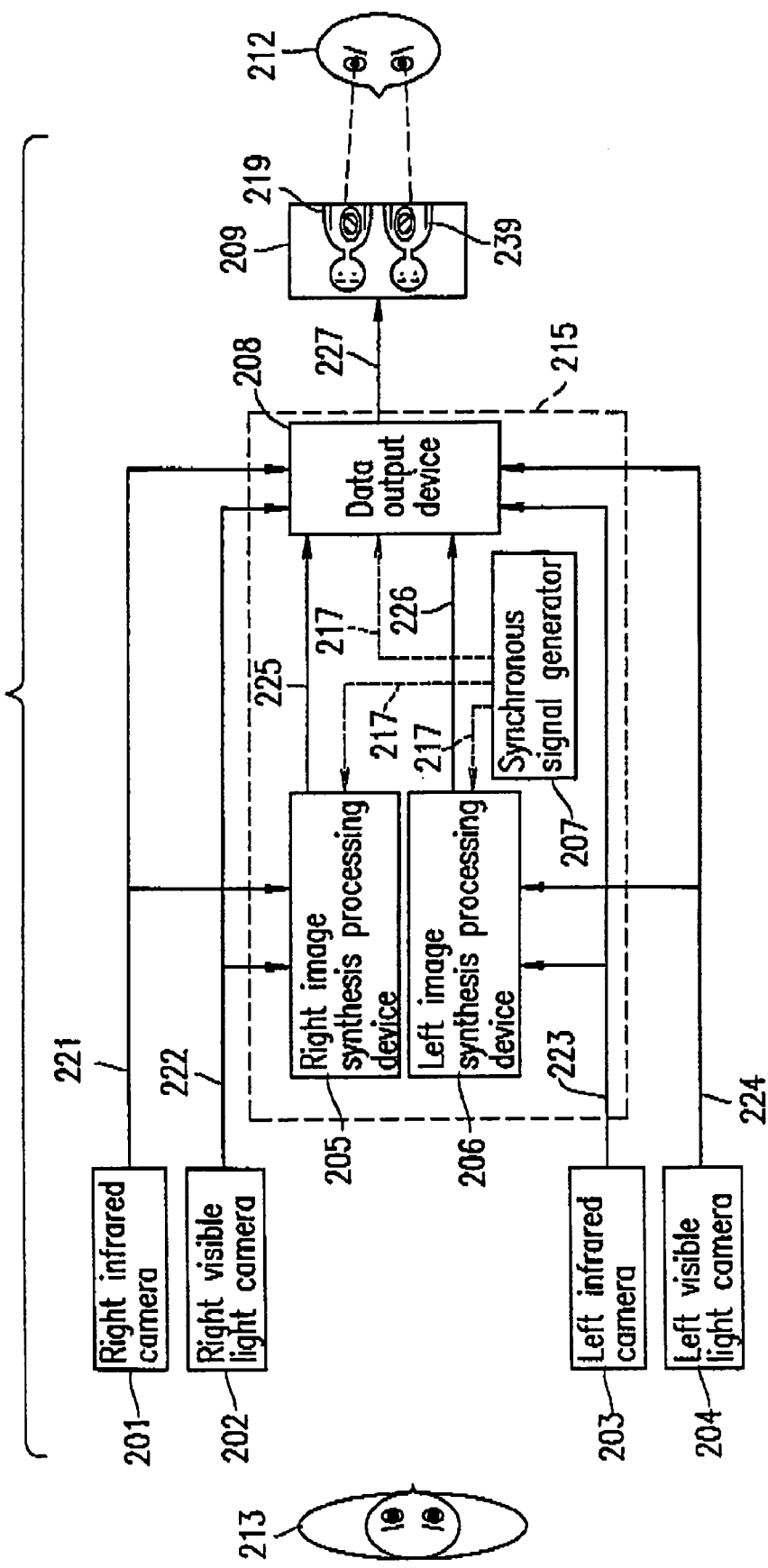

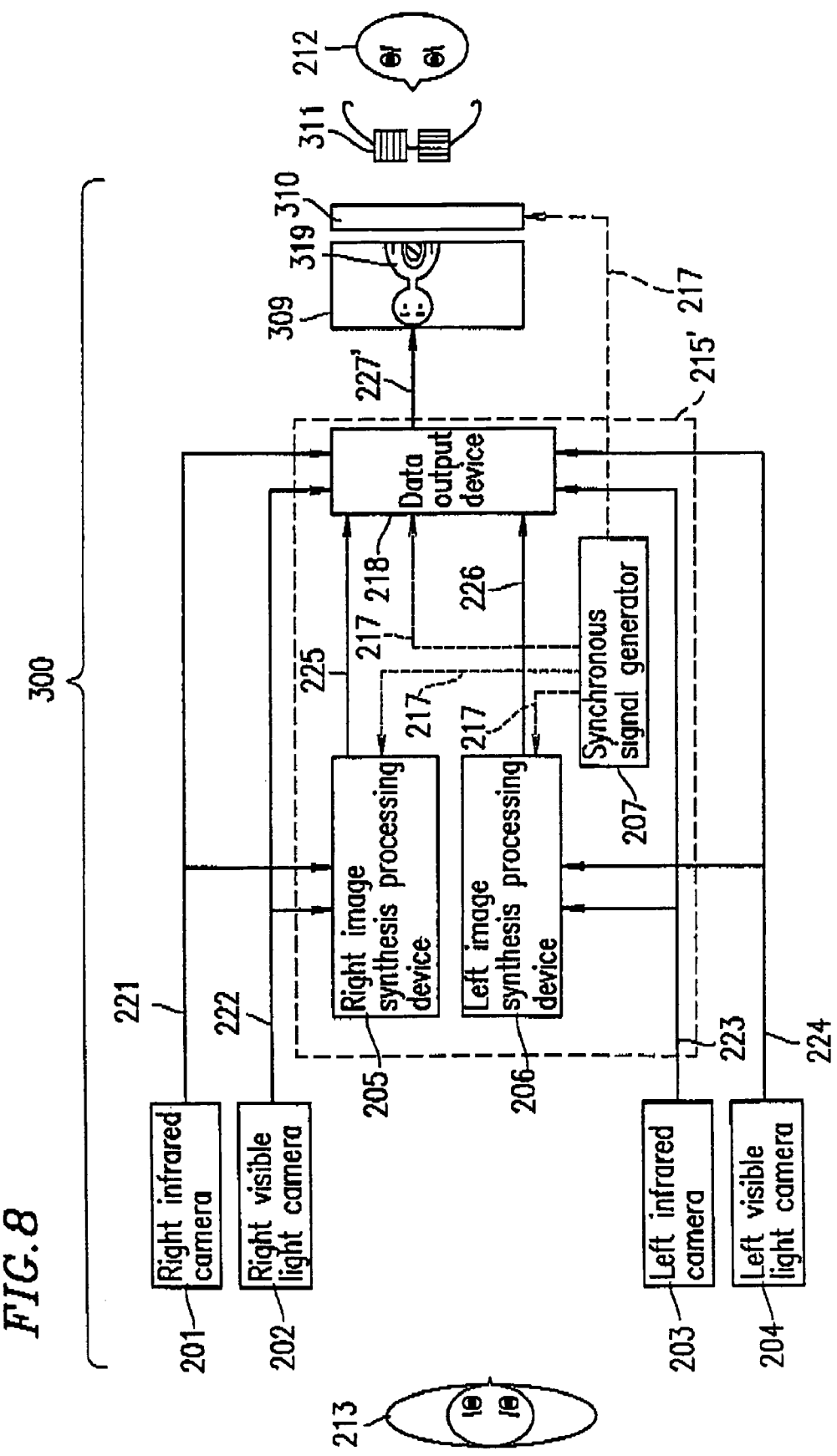

IMAGE SYNTHESIS APPARATUS

BACKGROUND OF THE INVENTION

1. Field of the Invention

The present invention relates to an image synthesis apparatus usable for observing a state of a surface of a subject having a temperature difference, for example, usable for diagnosing an inflammation site of a human body, and allowing a user to rapidly and accurately diagnose a site for diagnosis.

2. Description of the Related Art

FIG. 11 shows a structure of a conventional image synthesis apparatus 600 for generating a visible stereo image. The image synthesis apparatus 600 includes a left visible light camera 601 provided for imaging a subject from the left of the subject, a right visible light camera 602 provided for imaging the subject from the right of the subject, and a visible 3D (three-dimensional) image synthesis device 603. Conventionally, a visible stereo image is generated by synthesizing images obtained by the left visible light camera 601 and the right visible light camera 602 by the visible 3D image synthesis device 603.

An infrared camera is also conventionally used for diagnosing a site of a human body or other purposes. An infrared camera is used independently, and a physician diagnoses the site based on an image obtained by the infrared camera.

The use of a single infrared camera has a problem in that the obtained image is not as realistic as an actual visual observation, and thus sufficient information required for diagnosis is not obtained. Accordingly, the diagnosis of a subtle inflammation symptom relies heavily on the experience and intuition of the physician.

Japanese Laid-Open Publication No. 9-220203 discloses a diagnostic apparatus for synthesizing thermograph image information of a site for diagnosis and moire topograph information of the site. However, such a diagnostic apparatus merely provides a planar thermal image and cannot be used to rapidly and accurately grasp the state of the site for diagnosis.

SUMMARY OF THE INVENTION

According to one aspect of the invention, an image synthesis apparatus includes a right infrared camera and a left infrared camera; a right visible light camera and a left visible light camera; and a first image synthesis processing device for synthesizing data output from the right infrared camera and from the left infrared camera and data output from the right visible light camera and from the left visible light camera so that a three-dimensional thermal image and a three-dimensional visible light image are observed by an observer as overlapping each other.

In one embodiment of the invention, the first image synthesis processing device includes a synchronous signal generator for generating a synchronous signal; a second image synthesis processing device for synthesizing at least a portion of right infrared image data output from the right infrared camera and at least a portion of right visible light image data output from the right visible light camera in response to a synchronous signal generated by the synchronous signal generator so as to generate right synthesis image data; a third image synthesis processing device for synthesizing at least a portion of left infrared image data output from the left infrared camera and at least a portion of left visible light image data output from the left visible light camera in response to a synchronous signal generated by the synchronous signal generator so as to generate left synthesis image data; and a data output device for outputting the right synthesis image data and the left synthesis image data in a prescribed order in response to a synchronous signal generated by the synchronous signal generator.

In one embodiment of the invention, the second image synthesis processing device synthesizes a portion of the right infrared image data and the entire right visible light image data. The third image synthesis processing device synthesizes a portion of the left infrared image data and the entire left visible light image data.

In one embodiment of the invention, the image synthesis apparatus further includes a monitor for displaying a right synthesis image and a left synthesis image in a prescribed order based on the right synthesis image data and the left synthesis image data which are output from the data output device.

In one embodiment of the invention, the image synthesis apparatus further includes a polarizer for polarizing the right synthesis image in a first direction and polarizing the left synthesis image in a second direction different from the first direction, in response to a synchronous signal generated by the synchronous signal generator.

In one embodiment of the invention, the first image synthesis processing device includes a synchronous signal generator for generating a synchronous signal; and a data output device for outputting right infrared image data output from the right infrared camera, right visible light image data output from the right visible light camera, left infrared image data output from the left infrared camera, and left visible light image data output from the left visible light camera in a prescribed order, in response to a synchronous signal generated by the synchronous signal generator.

In one embodiment of the invention, the first image synthesis processing device includes a second image synthesis processing device for synthesizing right infrared image data output from the right infrared camera and left infrared image data output from the left infrared camera so as to generate three-dimensional thermal image data; a third image synthesis processing device for synthesizing right visible light image data output from the right visible light camera and left visible light image data output from the left visible light camera so as to generate three-dimensional visible light image data; and a fourth image synthesis processing device for synthesizing the three-dimensional thermal image data and the three-dimensional visible light image data so as to generate three-dimensional overall image data.

In one embodiment of the invention, the three-dimensional thermal image data includes a plurality of temperature levels, and a plurality of color tones are respectively assigned to the plurality of temperature levels.

In one embodiment of the invention, the three-dimensional overall image data includes three-dimensional coordinate data, and the three-dimensional overall image data is converted into two-dimensional data by transforming the three-dimensional coordinate data into two-dimensional coordinate data projected onto a prescribed plane in a three-dimensional coordinate space.

According to another aspect of the invention, an image synthesis apparatus includes a slit device including a plurality of slits; an infrared directing device for directing infrared toward a subject through the slit device; a plurality of infrared cameras provided in a direction substantially perpendicular to a direction in which the infrared is directed toward the subject; and an image synthesis processing device for synthesizing a plurality of thermal image data output from the plurality of infrared cameras so as to generate three-dimensional thermal image data.

In one embodiment of the invention, the image synthesis processing device generates the three-dimensional thermal image data based on a difference in shape between heat ray patterns reflected by the subject and respectively imaged by the plurality of infrared cameras.

Thus, the invention described herein makes possible the advantages of providing an image synthesis apparatus for allowing a user to rapidly and accurately grasp a state of a surf ace of a subject having a temperature difference and thus allowing a user to rapidly and accurately diagnose, for example, an inflammation site of a human body.

These and other advantages of the present invention will become apparent to those skilled in the art upon reading and understanding the following detailed description with reference to the accompanying figures.

BRIEF DESCRIPTION OF THE DRAWINGS

FIG. 4 is a schematic diagram illustrating a structure of an image synthesis apparatus according to a second example of the present invention;

FIG. 8 is a schematic diagram illustrating a structure of an image synthesis apparatus according to a third example of the present invention;

DESCRIPTION OF THE PREFERRED EMBODIMENTS

Figure 1:
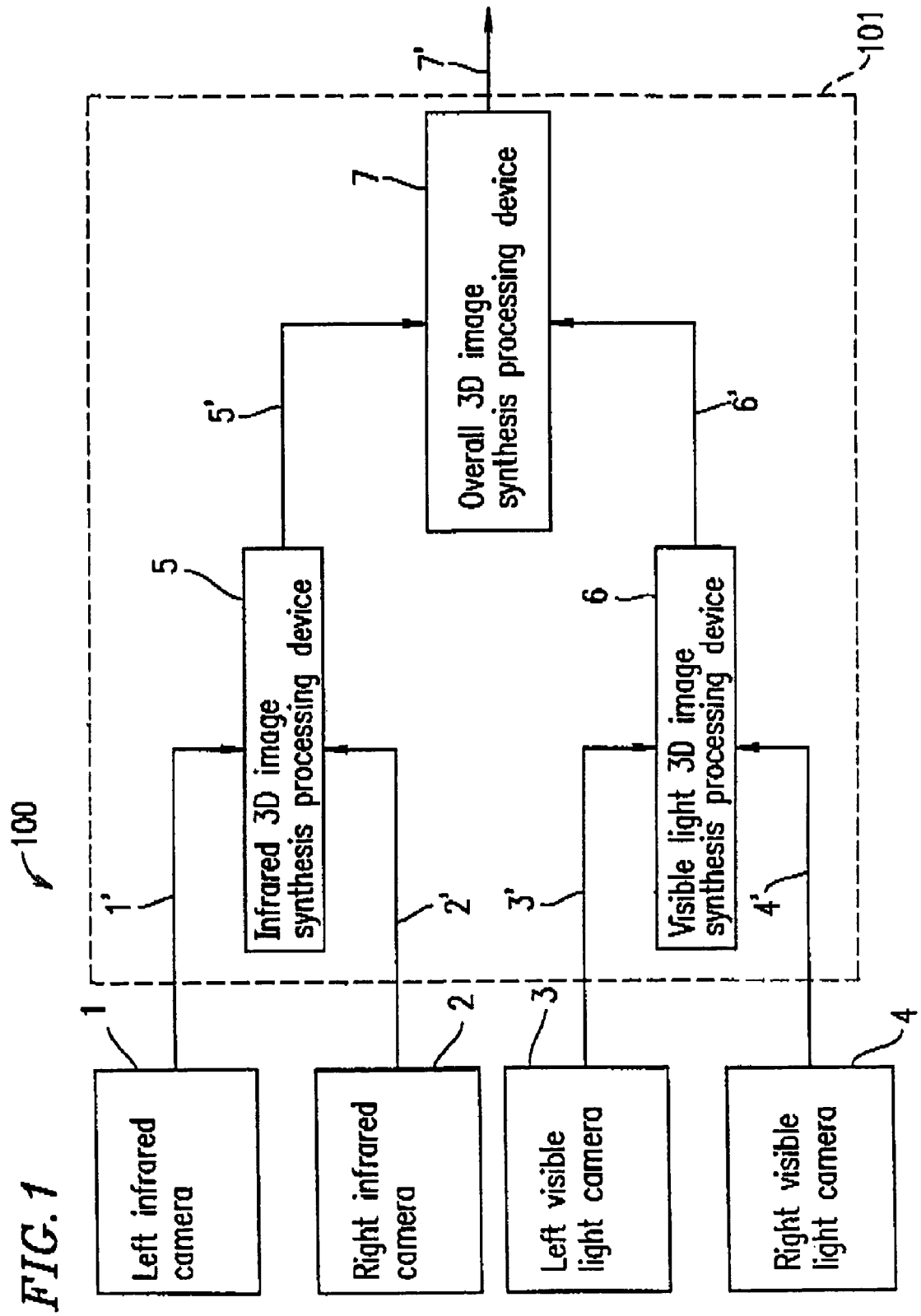
FIG. 1 is a schematic diagram illustrating a structure of an image synthesis apparatus according to a first example of the present invention.

Hereinafter, the present invention will be described by way of illustrative examples with reference to the accompanying drawings. Identical elements bear identical reference numerals in all the figures, and the descriptions thereof will be omitted.

EXAMPLE 1

FIG. 1 shows a structure of an image synthesis apparatus 100 according to a first example of the present invention. The image synthesis apparatus 100 is used for, for example, diagnosing an inflammation site of a human body as a subject of imaging.

The image synthesis apparatus 100 includes a left infrared camera 1, a right infrared camera 2, a left visible light camera 3, a right visible light camera 4, and an image synthesis processing device 101. The image synthesis processing device 101 includes an infrared 3D image synthesis processing device 5, a visible light 3D image synthesis processing device 6, and an overall 3D image synthesis processing device 7.

The left infrared camera 1 and the right infrared camera 2 respectively image a subject (not shown) from a left position corresponding to a left eye and a right position corresponding to a right eye, and thus generate infrared image data. The left visible light camera 3 and the right visible light camera 4 respectively image the subject from a left position corresponding to a left eye and a right position corresponding to a right eye, and thus generate visible light image data.

As shown in FIG. 1, left infrared image data 1' from the left infrared camera 1 and right infrared image data 2' from the right infrared camera 2 are input to the infrared 3D image synthesis processing device 5. Left visible light image data 3' from the left visible light camera 3 and right visible light image data 4' from the right visible light camera 4 are input to the visible light 3D image synthesis processing device 6.

The infrared 3D image synthesis processing device 5 generates 3D thermal image data 5' for each of the wavelength bands based on the left and right infrared image data 1' and 2'. Likewise, the visible light 3D image synthesis processing device 6 generates 3D visible light image data 6' for each of the wavelength bands based on the left and right visible light image data 3' and 4'. From the 3D thermal image data 5' and the 3D visible light image data 6, a 3D thermal image and a 3D visible light image are respectively generated as described below.

The 3D thermal image data 5' and the 3D visible light image data 6' are input to the overall 3D image synthesis processing device 7. The overall 3D image synthesis processing device 7 synthesizes the 3D thermal image data 5' and the 3D visible light image data 6', and thus generates overall 3D image data 7'. Namely, the overall 3D image data 7' includes the 3D thermal image data 5' synthesized with the 3D visible light image data 6'. From the overall 3D image data 7' an overall 3D image is obtained.

As described above, the image synthesis apparatus 100 generates an overall 3D image including a 3D visible light image synthesized with a 3D thermal image. Such an overall 3D image allows the user to grasp both the appearance and the thermal distribution in the site for diagnosis three-dimensionally. Therefore, the user can appreciate the site rapidly and accurately. Specifically, diagnosis of an inflammation site of a human body can be done rapidly and accurately since both an external symptom and the temperature distribution of a surface of the site are shown.

A greater number of infrared cameras and visible light cameras may be used (for example, four of each) in order to obtain a more precise 3D image.

Figure 2:
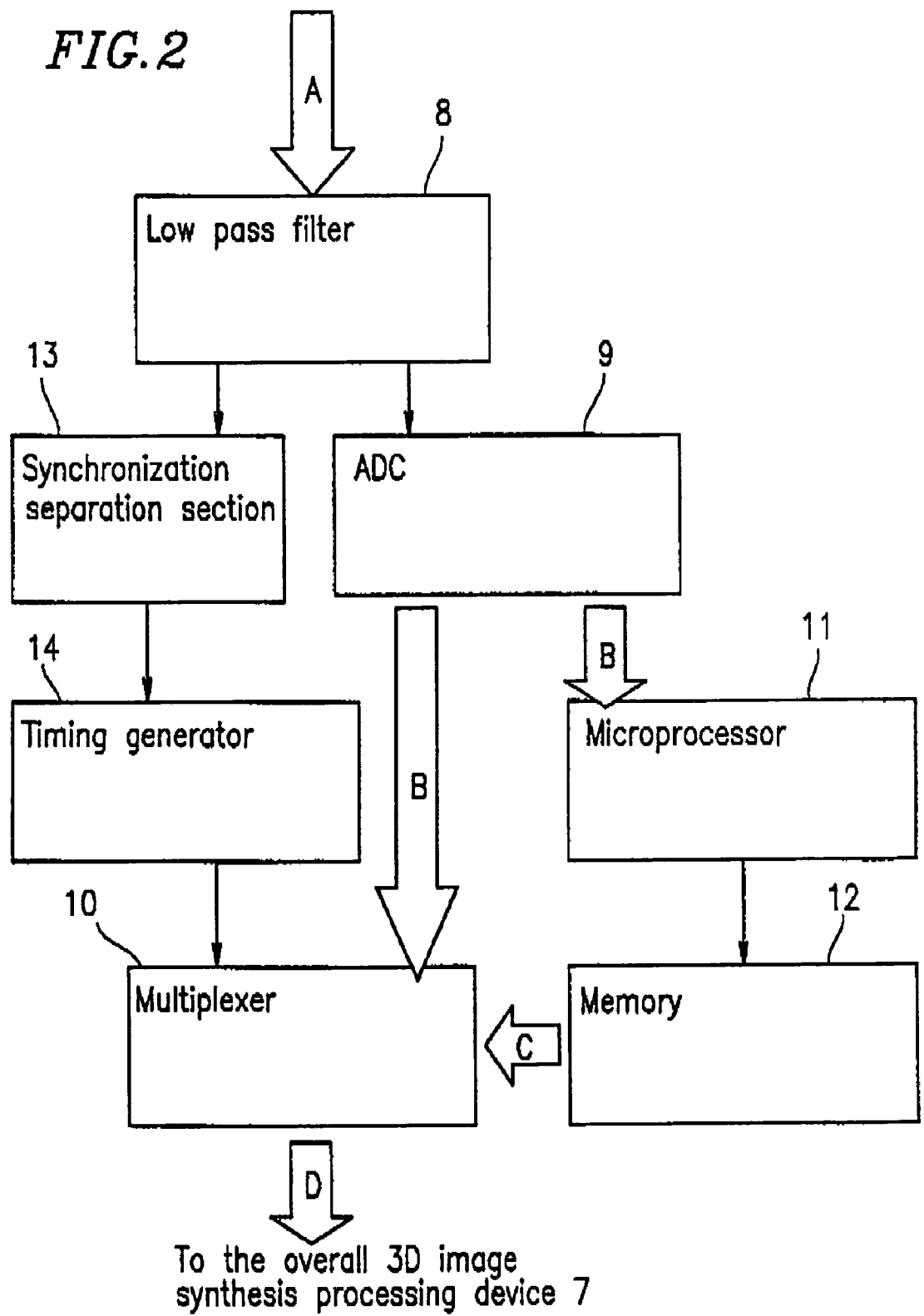
FIG. 2 is a diagram illustrating processing performed by an infrared 3D image synthesis processing device in the image synthesis apparatus shown in FIG. 1.

The data 1' and 2' obtained by the left and right infrared cameras 1 and 2 are analog data. The data 1' and 2' are processed by, for example, the infrared 3D image synthesis processing device 5. With reference to FIG. 2, an example of processing of data 1' performed by the infrared 3D image synthesis processing device 5 will be described. The data 2' is processed in substantially the same manner.

The left infrared image data 1' is input to a low pass filter 8. The low pass filter 8 removes an unnecessary high frequency component from the left infrared image data 1' to generate an analog left thermal image signal 8'. The analog left thermal image signal 8' is output to an ADC (analog to digital converter) 9 and a synchronous separation section 13.

The ADC 9 generates a digital left thermal image signal 31 from the analog left thermal image signal 8', and outputs the digital left thermal image signal 31 to a multiplexer 10 and a microprocessor 11. The microprocessor 11 reads a luminance signal level of the digital left thermal image signal 31, and specifies a digital color signal 32 to be added from a memory 12 in accordance with the luminance signal level.

The memory 12 has digital color signals 32 stored therein as a form of a color tone table. The digital color signals 32 respectively represent a great number of prescribed color tones. One of the color signals 32 specified by the microprocessor 11 is output to the multiplexer 10.

The multiplexer 10 has a horizontal and vertical retrace line period timing sent from a timing generator 14. The timing generator 14 generates the horizontal and vertical retrace line period timing based on a synchronous timing signal sent from the synchronous separation section 13. The multiplexer 10 outputs the digital left thermal image signal 31 or the digital color signal 32 based on the horizontal and vertical retrace line period timing. In this manner, the multiplexer 10 outputs a left color digital thermal image signal, instead of the digital color signal 32, in a period which is not the horizontal and vertical retrace line period.

The right infrared image data 2' is processed in substantially the same manner, and thus a right color digital thermal image signal is obtained. The 3D thermal image data 5' is generated from the left and right color digital thermal image signals, which is output to the overall 3D image synthesis processing device 7.

The luminance signal levels of the left infrared image data 1' and the right infrared image data 2' increase as the temperature rises. Utilizing this property, the luminance signal level of the analog left thermal image signal 8' (and an analog right thermal image signal) is detected. From the color tone table stored in the memory 12, a color tone is selected in accordance with the detected luminance signal level. The digital left thermal image signal 31 is colored by a digital color signal 32 representing the selected color tone. In other words, the thermal image is colored for each prescribed luminance signal level (i.e., for each prescribed temperature level data). Alternatively, a plurality of colors, for example, red, green, yellow and blue, may be assigned to each luminance signal level.

As described above, the 3D thermal image data 5', generated by the infrared 3D image synthesis processing device 5 in correspondence with the 3D visible light image data 6', is colored in accordance with the temperature level. Accordingly, the overall 3D image data 7' obtained by synthesizing the 3D thermal image data 5' and the 3D visible light image data 6' is also colored in accordance with the temperature level. Therefore, the obtained overall 3D image allows the user to easily understand the temperature distribution of the site for diagnosis three-dimensionally.

The data 7', which is a 3D image data, can be displayed two-dimensionally. This can be done by freely moving the data 7' by coordinate transformation in a virtual space by a computer and then projecting the data 7' onto a plane.

Figure 3:
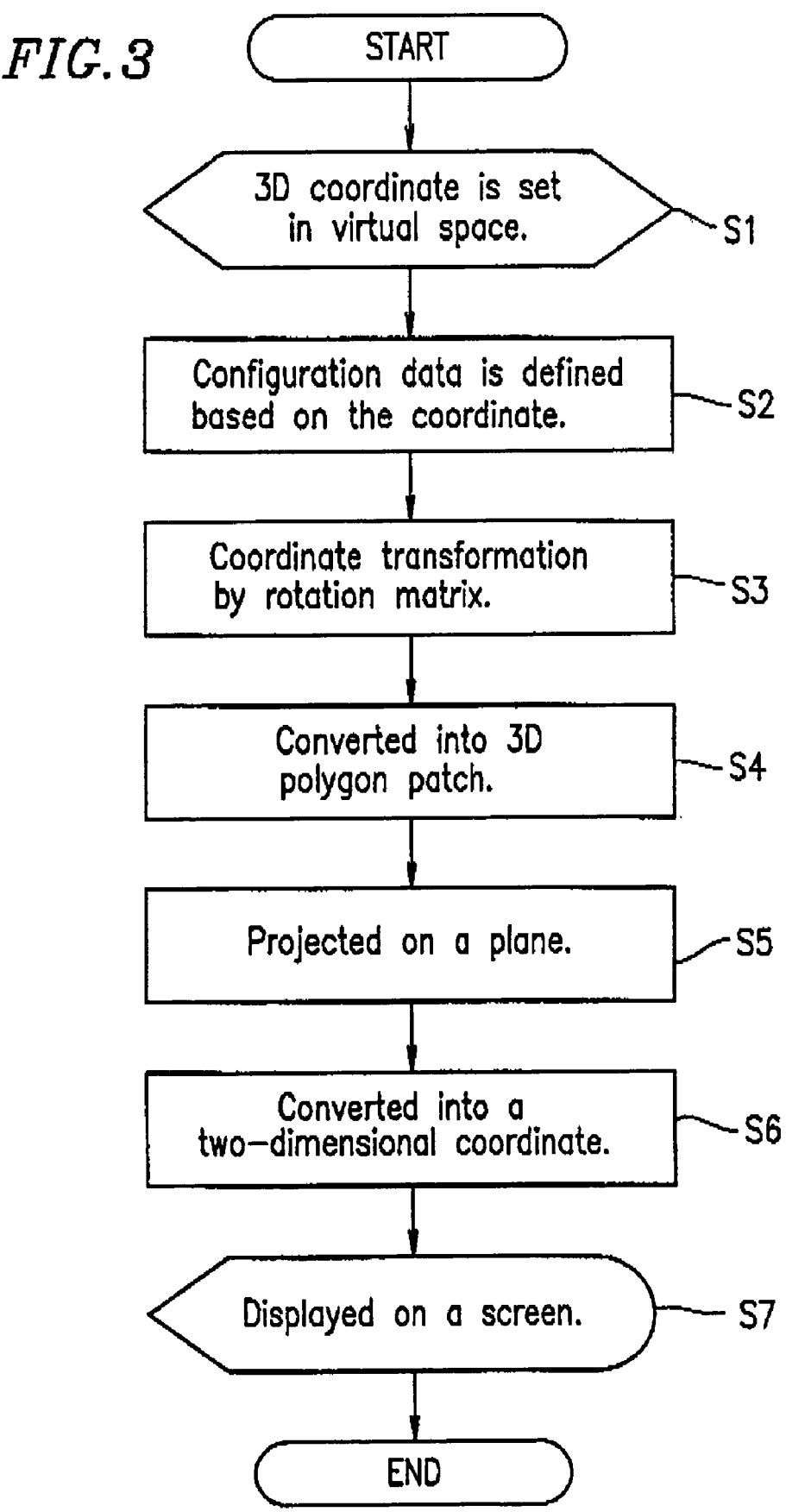
FIG. 3 is a flowchart illustrating an exemplary operation performed by the image synthesis apparatus shown in FIG. 1.

FIG. 3 is a flowchart illustrating an exemplary operation performed by a computer for realizing such a two-dimensional display. When the overall 3D image is obtained from the overall 3D image data 7', a 3D coordinate is set in a virtual space (world space) (step S1). Then, the coordinates of 3D image data of the overall 3D image are set, and thus configuration data is defined (step S2). When the coordinates of the overall 3D image are set in the 3D space, the overall 3D image is processed by rotation matrix to be coordinate-transformed (step S3).

Next, the configuration data of the coordinate-transformed overall 3D image is converted into a 3D polygon patch (step S4). The overall 3D image is projected onto an arbitrarily set plane, based on the configuration of the 3D polygon patch and the viewpoint of the user (step S5). Such processing converts the overall 3D image into a two-dimensional coordinate (step S6). The obtained two-dimensional image is displayed on a screen (step S7).

As described above, the image synthesis apparatus 100 according to the first example of the present invention can freely move an overall 3D image, obtained by synthesizing a 3D visible light image and a 3D thermal image, in a 3D space and represent an arbitrary 3D image as a two-dimensional image. Such a system allows the user to observe the site for diagnosis from a variety of aspects and thus to perform a more accurate diagnosis.

The overall 3D image synthesis processing device 7 may count the number of pixels of the overall 3D image data 7' which belong to the same temperature range, and calculate the volume of an arbitrary region in the site for diagnosis based on the obtained number. The arbitrary region is, for example, an inflammation site. By calculating the volume of the inflammation site each time the inflammation site is diagnosed, the physician can obtain an over-time change of the volume of the inflammation site (i.e., the degree of swelling) as specific numerical data.

EXAMPLE 2

FIG. 4 shows a structure of an image synthesis apparatus 200 according to a second example of the present invention.

The image synthesis apparatus 200 includes a right infrared camera 201, a right visible light camera 202, a left infrared camera 203, a left visible light camera 204, an image synthesis processing device 215, and a monitor 209. The image synthesis processing device 215 includes a right image synthesis processing device 205, a left image synthesis processing device 206, a synchronous signal generator 207, and a data output device 208.

The right infrared camera 201 and the left infrared camera 203 respectively image a subject 213 from a right position corresponding to a right eye and a left position corresponding to a left eye, and thus generate right infrared image data 221 and left infrared image data 223. The right visible light camera 202 and the left visible light camera 204 respectively image the subject 213 from a right position corresponding to a right eye and a left position corresponding to a left eye, and thus generate right visible light image data 222 and left visible light image data 224.

The right infrared image data 221 and the right visible light image data 222 are input to the right image synthesis processing device 205. In response to a synchronous signal 217 sent from the synchronous signal generator 207, the right image synthesis processing device 205 extracts the right infrared image data 221 and the right visible light image data 222 which were imaged at the same timing.

Figure 5A:
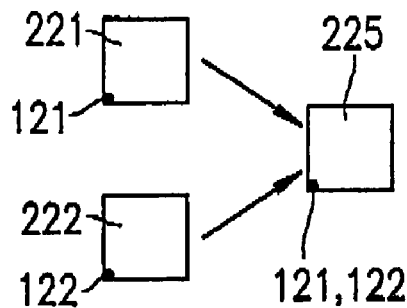
FIGS. 5A through 5D, 6, 7A and 7B are each a schematic view illustrating a data structure of data generated in the image synthesis apparatus shown in FIG. 2.

The right image synthesis processing device 205 generates right synthesis image data 225 as shown in FIG. 5A. The right infrared image data 221 and the right visible light image data 222 respectively have reference points 121 and 122. The right image synthesis processing device 205 causes the right infrared image data 221 and the right visible light image data 222 to overlap each other, so that the reference points 121 and 122 match each other. The right image synthesis processing device 205 can generate the right synthesis image data 225 by, for example, arranging pixels of the right infrared image data 221 and pixels of the right visible light image data 222 alternately.

Returning to FIG. 4, the left infrared image data 223 and the left visible light image data 224 are input to the left image synthesis processing device 206. In response to a synchronous signal 217 sent from the synchronous signal generator 207, the left image synthesis processing device 206 extracts the left infrared image data 223 and the left visible light image data 224 which were imaged at the same timing.

Figure 5B:
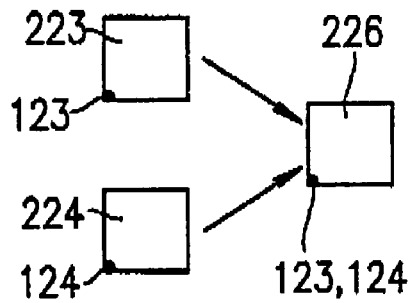

The left image synthesis processing device 206 generates left synthesis image data 226 as shown in FIG. 5B. The left infrared image data 223 and the left visible light image data 224 respectively have reference points 123 and 124. The left image synthesis processing device 206 causes the left infrared image data 223 and the left visible light image data 224 to overlap each other, so that the reference points 123 and 124 match each other. The left image synthesis processing device 206 can generate the left synthesis image data 226 by, for example, arranging pixels of the left infrared image data 223 and pixels of the left visible light image data 224 alternately.

Returning to FIG. 4, the right synthesis image data 225 and the left synthesis image data 226 are input to the data output device 208. In response to a synchronous signal 217 sent from the synchronous signal generator 207, the data output device 208 outputs the right synthesis image data 225 and the left synthesis image data 226 to the monitor 209 in a prescribed order (for example, alternately) as overall synthesis image data 227.

Figure 5C:
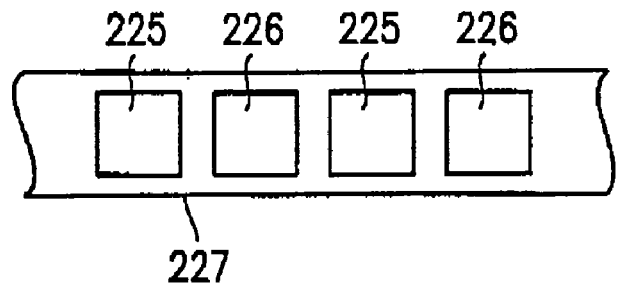

FIG. 5C shows a data structure of the overall synthesis image data 227 including the right synthesis image data 225 and the left synthesis image data 226 arranged alternately. The overall synthesis image data 227 includes instruction data for instructing the monitor 209 to generate a right synthesis image 219 from a plurality of right synthesis image data 225 output from the output device 208 as shown in FIG. 5C, to generate a left synthesis image 239 from a plurality of left synthesis image data 226 also output from the output device 208 as shown in FIG. 5C, and to display the right synthesis image 219 and the left synthesis image 239 side by side as shown in FIG. 4.

The monitor 209 receives the right synthesis image data 225, the left synthesis image data 226 and the instruction data, and displays the right synthesis image 219 and the left synthesis image 239 side by side. A user or observer 212 looks at the right synthesis image 219 with the right eye and looks at the left synthesis image 239 with the left eye, and thus perceives an overall 3D image including a 3D thermal image and a 3D visible light image overlapping each other.

Figure 5D:
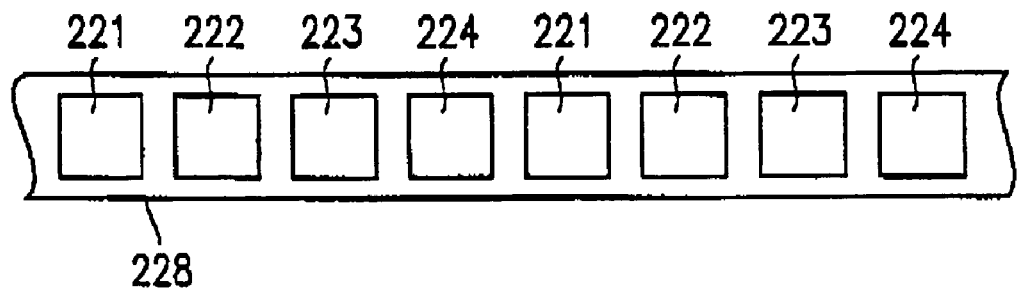

FIG. 5D shows a data structure of alternative overall synthesis image data 228. The overall synthesis image data 228 may be output to the monitor 209 instead of the overall synthesis image data 227. The overall synthesis image data 228 includes the right infrared image data 221, the right visible light image data 222, the left infrared image data 223 and the left visible light image data 224 arranged in this order repetitiously. In order to obtain the overall synthesis image data 228, the right infrared image data 221, the right visible light image data 222, the left infrared image data 223 and the left visible light image data 224 are directly input to the data output device 208 without being synthesized by the right and left image synthesis processing section 205 and 206. The data output device 208 arranges the data 221 through 224 as shown in FIG. 5D based on a synchronous signal 217 sent from the synchronous signal generator 207. The overall synthesis image data 228 is output based on a synchronous signal 217, and the monitor 209 displays the overall synthesis image data 228.

As described above, the image synthesis apparatus 200 according to the second example of the present invention provides the right synthesis image data 225 and the left synthesis image data 226 to the user 212 in the form of the overall synthesis image data 227. Alternatively, the image synthesis apparatus 200 can provide the right infrared image data 221, the right visible light image data 222, the left infrared image data 223, and the left visible light image data 224 to the user 212 in the form of the overall synthesis image data 228.

In either case, the user 212 sees a 3D thermal image (obtained by synthesizing the right infrared image data 221 and the left infrared image data 223) and a 3D visible light image (obtained by synthesizing the right visible light image data 222 and the left visible light image data 224) as overlapping each other. As a result, the user can perceive the two images, i.e., the 3D thermal image and the 3D visible light image, as one synthesized image.

Thus, the image synthesis apparatus 200 in the second example provides an effect which is equivalent of the effect of the image synthesis apparatus 100 shown in FIG. 1, i.e., the user perceives the synthesized image he/she sees as being the same as an overall 3D image generated by synthesizing the 3D thermal image data 5' and the 3D visible light image data 6' by the overall 3D image synthesis processing section 7.

Figure 6:
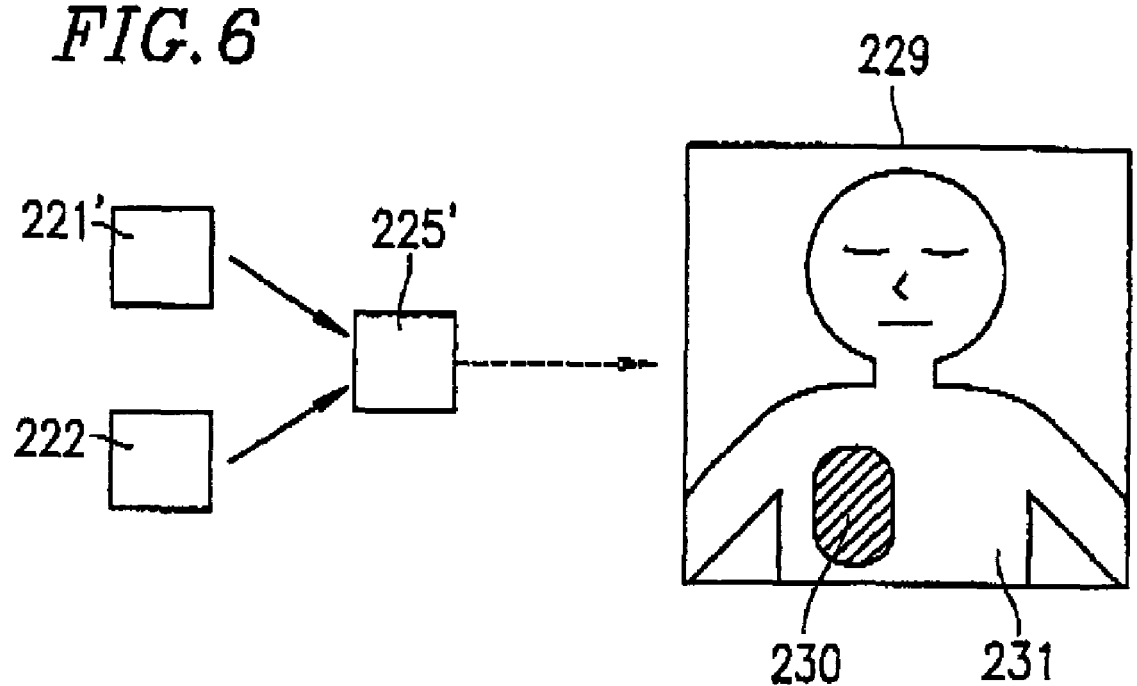

Alternatively, as shown in FIG. 6, the right image synthesis processing section 205 (FIG. 4) may synthesize a portion 221' of the right infrared image data 221 and the entire right visible light image data 222 to generate right synthesis image data 225'. The right synthesis image data 225' can be generated by overlapping the portion 221' of the right infrared image data 221 with the entire right visible light image data 222 having a light luminance or intensity thereof being partially lowered. From the right synthesis image data 225', a right synthesis image 229 is obtained. A part of the right synthesis image 229 is a thermal image 230 based on the portion 221', and the rest of the right synthesis image 229 is a visible light image 231 based on the right visible light image data 222. The left image synthesis processing section 206 may perform the same processing.

Alternatively, the portion 221' of the right infrared image data 221 and a portion (not shown) of the right visible light image data 222 may overlap each other.

Referring to FIG. 4 again, when a physician as the user or observer 212 diagnoses a patient as the subject 231, the physician can predict the position of an inflammation site based on the symptoms of the patient and the physician's own experience. In such a case, the thermal image 230 can be shown for only the predicted position and the vicinity thereof while the visible light image 231 is shown for the rest. This way, the physician can grasp the accurate inflammation site by the visible light image 231 and can accurately grasp the fever site at the inflammation site by the thermal image 230 at the same time.

The area of the human body in which the thermal image 230 is displayed may be an area having a threshold temperature which is set by the user or higher, or the threshold temperature or lower. Such an area may be changed by the intention of the user.

As the synchronous signal generator 207, any timing circuit is usable.

Figure 7A:
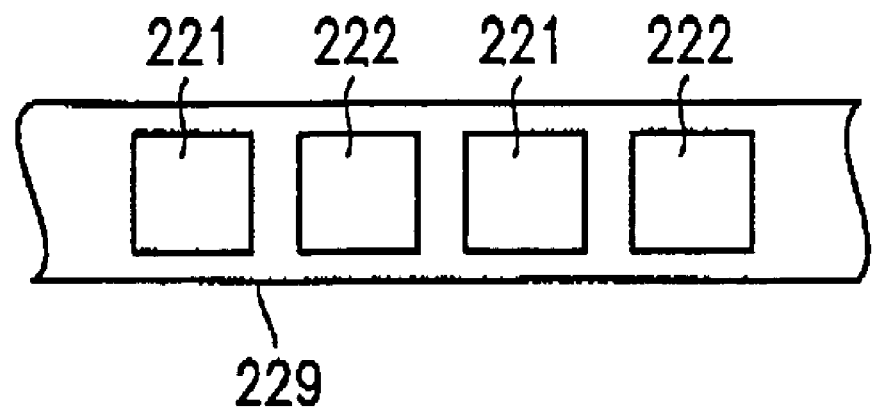
Figure 7B:
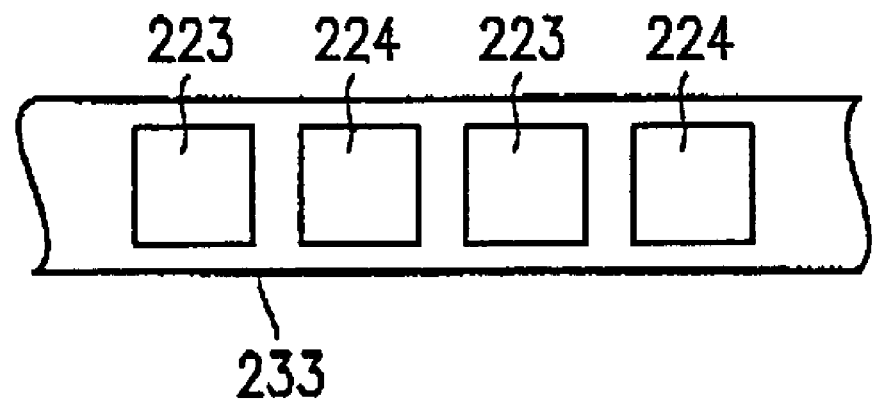

Instead of the monitor 209, a pair of right and left monitors may be used. In this case, the right synthesis image data 225 is input to the right monitor, and the left synthesis image data 226 is input to the left monitor. Alternatively, right synthesis image data 229 having a data structure shown in FIG. 7A may be input to the right monitor. The right synthesis image data 229 includes the right infrared image data 221 and the right visible light image data 222 arranged alternately. The right monitor displays a right infrared image and a right visible light image alternately. The alternating display of the right infrared image and the right visible light image is perceived by the user as being the same as the display of the right synthesis image 219 (FIG. 4). Likewise, left synthesis image data 233 having a data structure shown in FIG. 7B may be input to the left monitor. The alternating display of the left infrared image and the left visible light image is perceived by the user as being the same as the display of the left right synthesis image 239 (FIG. 4).

Instead of the monitor 209, a monitor of a head mount type (for example, goggles type) including two liquid crystal displays, i.e., for the right eye and the other for the left eye may be used.

EXAMPLE 3

FIG. 8 shows a structure of an image synthesis apparatus 300 according to a third example of the present invention.

The image synthesis apparatus 300 includes an image synthesis processing section 215', a monitor 309, and a polarizer 310 in addition to the right infrared camera 201, the right visible light camera 202, the left infrared camera 203, and the left visible light camera 204. The image synthesis processing section 215' includes a right image synthesis processing section 205, a left image synthesis processing section 206, a synchronous signal generator 207, and a data output device 218 for outputting overall synthesis image data 227' to the monitor 309. The overall synthesis image data 227' has the same data structure as that of the overall synthesis image data 227 shown in FIG. 5C, except that the overall synthesis image data 227' includes instruction data for instructing the monitor 309 to display the right synthesis image data 225 and the left synthesis image data 226 as a right-left synthesized image 319. Except for the above-mentioned points, the image synthesis apparatus 300 has substantially the same structure as that of the image synthesis apparatus 200 shown in FIG. 4.

The monitor 309 receives the right synthesis image data 225 and the left synthesis image data 226 which are output alternately from the output device 218, as well as the instruction data. The monitor 309 alternately displays a right synthesis image based on the right synthesis image data 225 and a left synthesis image based on the left synthesis image 226, and the observer 212 perceives the two images alternately output as the left-right synthesized image 319.

The polarizer 310 includes a well known liquid crystal device or the like. In response to a synchronous signal 217 from the synchronous signal generator 207, the polarizer 310 polarizes the right synthesis image in a first prescribed direction and polarizes the left synthesis image in a second prescribed direction which is different from the first prescribed direction. After the polarization, the polarization directions of the right synthesis image and the left synthesis image are different at, for example, 90° from each other. The observer 212 observes the right synthesis image and the left synthesis image, polarized in different directions, through polarization glasses 311. The observer 212 sees the right synthesis image with his/her right eye and the left synthesis image with his/her left eye, and thus perceives the 3D thermal image and the 3D visible light image as one overall 3D image.

In the third example, the observer 212 is allowed to perceive the overall 3D image using the right-left synthesized image 319, the polarizer 310, and the polarization glasses 311. The observer 212 can perceive the overall 3D image in other manners. For example, a lenticular screen can be used. In this case, the right and left synthesis images are each divided into a plurality of portions along grooves of the lenticular screen. The right-left synthesized image 319 is perceived as the resultant plurality of portions of the right and left synthesis images which are arranged alternately.

EXAMPLE 4

Figure 9:
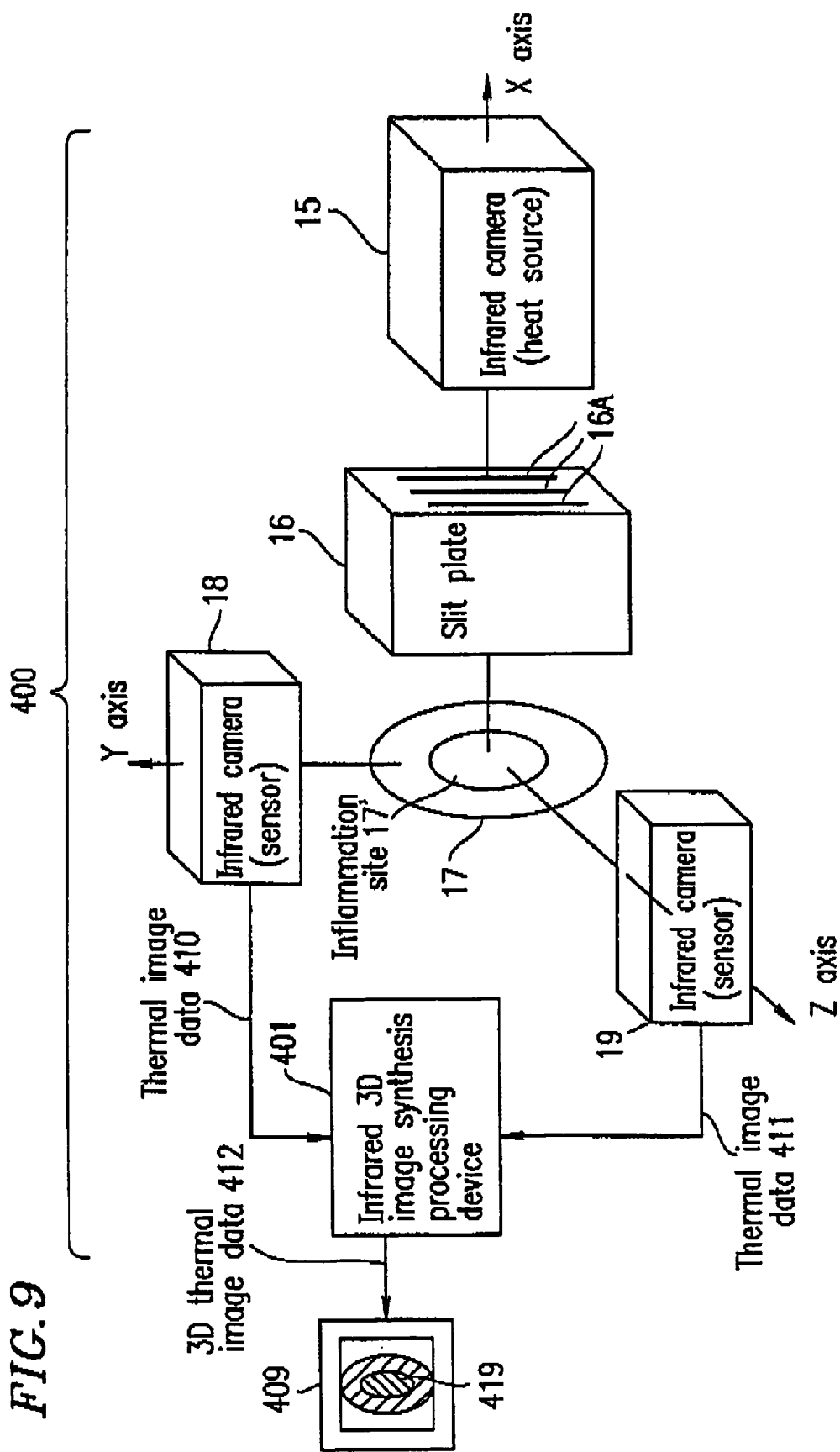
FIG. 9 is a schematic diagram illustrating a structure of an image synthesis apparatus according to a fourth example of the present invention.

FIG. 9 shows a structure of an image synthesis apparatus 400 according to a fourth example of the present invention.

The image synthesis apparatus 400 includes an infrared camera 15 used as a heat source, a slit plate 16, infrared cameras 18 and 19 used as sensors, and an infrared 3D image synthesis processing device 401.

The infrared cameras 18 and 19 for imaging a subject 17 are respectively provided on Y and Z axes, which pass through the subject 17 and are perpendicular to each other. The infrared cameras 18 and 19 are of a passive type for sensing infrared and thus generating a thermal image. The infrared cameras 18 and 19 provide thermal image data of the subject 17.

The slit plate 16 having a plurality of slits 16A extended in the direction of the Y axis is provided on an X axis which is perpendicular to both the Y and Z axes. The infrared camera 15 is provided so as to face the subject 17 with the slit plate 16 being therebetween. The infrared camera 15 is of an active type for directing infrared toward a subject and imaging the subject based on the light reflected by the subject. Infrared emitted by the infrared camera 15 is directed to the subject 17 through the slits 16A of the slit plate 16. Instead of the infrared camera 15, any device for directing infrared toward a subject is usable.

Figure 10A:
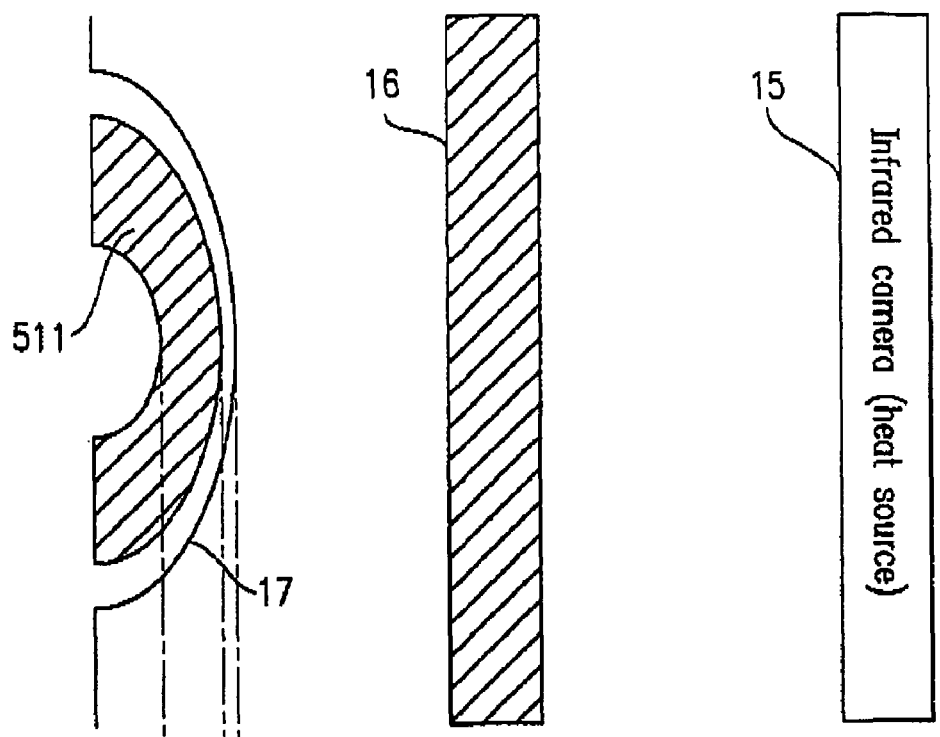
FIGS. 10A and 10B show heat ray patterns obtained in the image synthesis apparatus shown in FIG. 9.
Figure 10B:
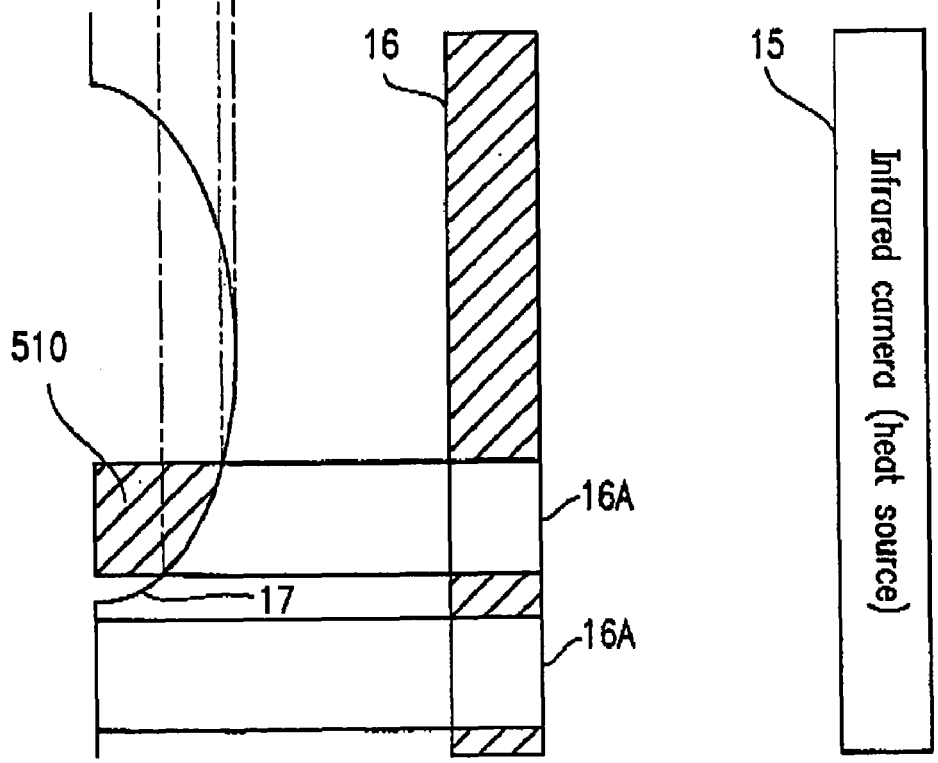
Figure 11:
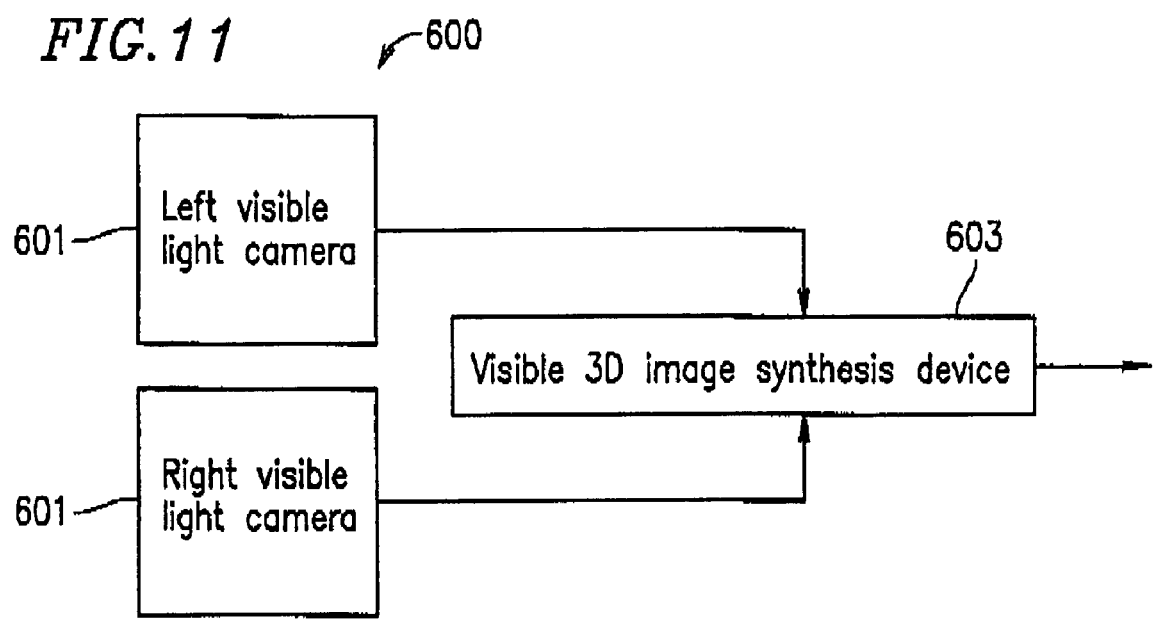
FIG. 11 is a block diagram illustrating a conventional image synthesis apparatus.

With reference to FIGS. 9, 10A and 10B, infrared emitted by the infrared camera 15 passes through the slits 16A extended parallel to the Y axis, and are directed to the subject 17 as heat rays parallel to the X axis.

In one example, it is assumed that the subject 17 has a hemispheric projection as shown in FIGS. 10A and 10B. In the case where the subject 17 is imaged by the infrared camera 18 in the direction of the Y axis to which the slits 16A are parallel, a linear heat ray pattern 510 as shown in FIG. 10B is obtained. In the case where the subject 17 is imaged by the infrared camera 19 in the direction of the Z axis perpendicular to the X axis and the Y axis, a curved heat ray pattern 511 as shown in FIG. 10A is obtained. The curves of the heat ray pattern 511 have different curvatures depending on the position of the curved surface of the subject 17. The infrared cameras 18 and 19 image infrared emitted by the subject 17 itself in addition to the patterns 510 and 511. Thus, temperature level data representing the temperature distribution of the surface of the subject 17 is obtained.

Thermal image data 410 having the heat ray pattern 510 output by the infrared camera 18, which images the subject 17 in the direction of the Y axis, and thermal image data 411 having the heat ray pattern 511 output by the infrared camera 19, which images the subject 17 in the direction of the Z axis, are input to infrared 3D image synthesis processing device 401.

The infrared 3D image synthesis processing device 401 generates 3D thermal image data 412 based on the difference in shape between the heat ray patterns 510 and 511. The 3D thermal image data 412 can be generated by, for example, using a well known technology for generating 3D topological data from two-dimensional contours. A virtual 3D thermal image 419 obtained from the 3D thermal image data 412 is displayed on a screen 409. The 3D thermal image data 412 is colored for each temperature level data, and thus the virtual 3D thermal image 419 shows a temperature distribution of the surface of the subject 17.

The image synthesis apparatus 400 in the fourth example provides the virtual 3D thermal image 419 of the subject 17 based on the difference in shape between the heat ray patterns 510 and 511. Accordingly, a 3D image of the subject 17 can be provided without requiring visible light image data output by a visible light camera.

Since the virtual 3D thermal image 419 is obtained based on the thermal image data 410 and 411 having data on the shape and the temperature distribution of the subject 17, the site for diagnosis of the subject 17 can be rapidly and accurately observed.

The image synthesis apparatus 400 may include three or more infrared cameras for imaging the subject 17. In this case, the plurality of infrared cameras are preferably provided on a plane including the Y axis and the Z axis.

The thermal image data 410 and 411 may be synthesized with visible light image data obtained by a pair of visible light cameras (not shown) to generate an overall 3D image.

As described in the first example, the virtual 3D thermal image 419 may be appropriately moved in a 3D space.

The infrared 3D image synthesis processing device 401 may count the number of pixels of the 3D thermal image data 412 which belong to the same temperature range and calculate the volume of an arbitrary region in the subject 17 based on the obtained number. The arbitrary region is, for example, an inflammation site. By calculating the volume of the inflammation site each time the inflammation site is diagnosed, the physician can obtain an over-time change of the volume of the inflammation site (i.e., the degree of swelling) as specific numerical data.

According to the present invention, the subject of imaging is not limited to a human body. The present invention is applicable to imaging of, for example, creatures including animals and plants, machines or other structures, and scenery including mountains, oceans and cityscapes.

According to the present invention, overall 3D image data is generated by synthesizing 3D thermal image data and 3D visible light image data of a subject. Therefore, a 3D visible light image of the subject similar to the image obtained by visual observation is displayed together with a thermal image. Diagnosis of a site of the subject an be rapidly and accurately performed. The present invention is specifically suitable to diagnosis of an inflammation site of a human body.

In one embodiment of the invention, infrared is directed to the subject through slits, and thus thermal image data of the subject can be obtained in a prescribed direction. Without a visible light camera, both thermal data and data on the external shape of the subject are obtained. Therefore, diagnosis of a site of the subject can be rapidly and accurately performed.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An image synthesis apparatus, comprising:
   a right infrared camera and a left infrared camera;
   a right visible light camera and a left visible light camera; and
   a first image synthesis processing device for synthesizing data output from the right infrared camera and the left infrared camera and data output from the right visible light camera and the left visible light camera so that a three-dimensional thermal image and a three-dimensional visible light image are observed by an observer as overlapping each other,
   wherein the three-dimensional thermal image comprises a plurality of color tones having a predetermined correspondence with a luminance represented by the data output from the right infrared camera and the data output by the left infrared camera,
   wherein a temperature of a subject can be inferred by the observer based on the predetermined color correspondence.

2. An image synthesis apparatus according to claim 1, wherein the first image synthesis processing device includes:
   a synchronous signal generator for generating a synchronous signal;
   a second image synthesis processing device for synthesizing at least a portion of right infrared image data output from the right infrared camera and at least a portion of right visible light image data output from the right visible light camera in response to a synchronous signal generated by the synchronous signal generator so as to generate right synthesis image data;
   a third image synthesis processing device for synthesizing at least a portion of left infrared image data output from the left infrared camera and at least a portion of left visible light image data output from the left visible light camera in response to a synchronous signal generated by the synchronous signal generator so as to generate left synthesis image data; and
   a data output device for outputting the right synthesis image data and the left synthesis image data in a prescribed order in response to a synchronous signal generated by the synchronous signal generator.

3. An image synthesis apparatus according to claim 2, wherein:
   the second image synthesis processing device synthesizes a portion of the right infrared image and the entire right visible light image data, and
   the third image synthesis processing device synthesizes a portion of the left infrared image data and the entire left visible light image data.

4. An image synthesis apparatus according to claim 2, further comprising a monitor for displaying a right synthesis image and a left synthesis image in a prescribed order based on the right synthesis image data and the left synthesis image data which are output from the data output device.

5. An image synthesis apparatus according to claim 4, further comprising a polarizer for polarizing the right synthesis image in a first direction and polarizing the left synthesis image in a second direction different from the first direction, in response to a synchronous signal generated by the synchronous signal generator.

6. An image synthesis apparatus according to claim 1, wherein the first image synthesis processing device includes:
   a synchronous signal generator for generating a synchronous signal; and
   a data output device for outputting right infrared image data output from the right infrared camera, right visible light image data output from the right visible light camera, left infrared image data output from the left infrared camera, and left visible light image data output from the left visible light camera in a prescribed order, in response to a synchronous signal generated by the synchronous signal generator.

7. An image synthesis apparatus according to claim 1, wherein the first image synthesis processing device includes:
- a second image synthesis processing device for synthesizing right infrared image data output from the right infrared camera and left infrared image data output from the left infrared camera so as to generate three-dimensional thermal image data;
- a third image synthesis processing device for synthesizing right visible light image data output from the right visible light camera and left visible light image data output from the left visible light camera so as to generate three-dimensional visible light image data; and
- a fourth image synthesis processing device for synthesizing the three-dimensional thermal image data and the three-dimensional visible light image data so as to generate three-dimensional overall image data.

8. An image synthesis apparatus according to claim 7, wherein the three-dimensional thermal image data includes a plurality of temperature levels, and the plurality of color tones are respectively assigned to the plurality of temperature levels.

9. An image synthesis apparatus according to claim 7, wherein the three-dimensional overall image data includes three-dimensional coordinate data, and the three-dimensional overall image data is converted into two-dimensional data by transforming the three-dimensional coordinate data into two-dimensional coordinate data projected onto a prescribed plane in a three-dimensional coordinate space.

10. An image synthesis apparatus, comprising:
- a slit device including a plurality of slits;
- an infrared directing device for directing infrared toward a subject through the slit device;
- a plurality of infrared cameras provided in a direction substantially perpendicular to a direction in which the infrared is directed toward the subject;
- a plurality of visible light cameras provided in a direction substantially perpendicular to a direction in which the visible light images a subject; and
- an image synthesis processing device for synthesizing a plurality of thermal image data output from the plurality of infrared cameras so as to generate three-dimensional thermal image data, and
- said image synthesis processing device synthesizing a plurality of visible light image data from the plurality of visible light cameras so as to generate three-dimensional visible light image data,
- wherein the three-dimensional thermal image data comprises a plurality of color tones having a predetermined correspondence with a luminance represented by the data output from the plurality of infrared cameras,
- wherein a temperature of the subject can be inferred by the observer based on the predetermined color correspondence.

11. An image synthesis apparatus according to claim 10, wherein the image synthesis processing device generates the three-dimensional thermal image data based on a difference in shape between heat ray patterns reflected by the subject and respectively imaged by the plurality of infrared cameras.

* * * * *